United States Patent [19]
Lee et al.

[11] Patent Number: 5,276,199
[45] Date of Patent: Jan. 4, 1994

[54] PROCESS FOR PREPARING CYCLOPENTENONES

[75] Inventors: John Y. Lee; Meng-Sheng Ao; Stephen E. Belmont, all of Baton Rouge, La.

[73] Assignee: Ethyl Corporation, Richmond, Va.

[21] Appl. No.: 16,447

[22] Filed: Feb. 11, 1993

[51] Int. Cl.$^5$ ............................................. C07C 45/74
[52] U.S. Cl. .................................... 568/350; 568/379
[58] Field of Search ............... 568/353, 343, 345, 346, 568/388, 366

[56] References Cited

U.S. PATENT DOCUMENTS

| | | | |
|---|---|---|---|
| 3,907,896 | 9/1975 | Calame et al. | 568/350 |
| 4,384,144 | 5/1983 | Shono et al. | 568/347 |
| 4,413,145 | 11/1983 | Piancatelli et al. | 568/353 |
| 5,026,919 | 6/1991 | Dessau | 568/353 |

OTHER PUBLICATIONS

Rosini G., et al., "A New Route to 1,4-Diketones and its Application to (Z)-Jasmone and Dihydrojasmone Synthesis", *Tetrahedron* vol. 39, No. 24, pp. 4127–4132 (1983).

Acheson, R. M., et al., "Experiments Bearing on the Synthesis of Cortisone, Part I,* Some Cyclopentenone Derivatives", *J. Chem. Soc.*, pp. 1127∝1133 (1952).

*Primary Examiner*—James H. Reamer
*Attorney, Agent, or Firm*—David M. Bunnell

[57]     ABSTRACT

A process for preparing a cyclopentenone by forming a two-phase mixture of a 1,4-diketone, a water immiscible organic solvent, and an aqueous base solution, and heating the mixture so as to convert the 1,4-diketone to a cyclopentenone which collects in the organic solvent phase.

11 Claims, No Drawings

PROCESS FOR PREPARING CYCLOPENTENONES

This process relates generally to the preparation of cyclic ketones and more specifically to the preparation of hydrocarbyl substituted cyclopentenones from 1,4-diketones.

Cyclopentenones are useful compounds for preparing hydrocarbyl substituted cyclopentadienes which can be reacted with transition metal salts to form metallocene catalysts for olefin polymerization. It is known to make cyclopentenones, such as 3-methylcyclopent-2-en-1-one, by heating a 1,4-diketone, such as acetonylacetone, with base, such as NaOH. The product is unstable in the presence of base. Consequently, either care must be taken to avoid excessive tar formation or the product must be removed as it is formed, for example, by distillation as described in U.S. Pat. No. 3,907,896.

We have now discovered an improved process for preparing cyclopentenones, which can be carried out at lower temperatures and does not involve the contemporaneous removal of product from the reaction mixture. This invention also provides a practical process in which the reactor-loading can be 5-10 times higher than in the process according to the above mentioned patent.

In accordance with this invention there is provided a process for preparing a cyclopentenone, which process comprises forming a two-phase mixture of a 1,4-diketone, a water immiscible organic solvent and an aqueous base solution, and heating the mixture so as to convert the 1,4-diketone to a cyclopentenone which collects in the organic solvent phase.

The 1,4-diketone reactants for use in the process of the invention can be prepared as known in the art, for example, see Rosini G. et al. *Tetrahedron*, 39 (24) 4127-32 (1983).

Preferred 1,4-diketones have the formula $CH_2COCH_2CH_2COCH_2R$ where R is hydrogen or a hydrocarbyl group which contains 1 to 15 carbon atoms. Non-limiting examples of hydrocarbyl groups include alkyl, substituted alkyl, aryl, substituted aryl, alkenyl, substituted alkenyl, and the like such as methyl, ethyl, propyl, isopropyl, butyl, isobutyl, tert-butyl, pentyl, hexyl, cyclohexyl, pentenyl, benzyl, phenyl, and naphthyl.

The reaction mixture is a two-phase system which includes an aqueous phase and an organic solvent phase.

The aqueous phase comprises an aqueous solution of a base such as an alkali metal hydroxide solution, for example, sodium or potassium hydroxide. Preferably, sodium hydroxide is used in amounts to provide a 0.5 to 5 molar aqueous NaOH solution.

The organic solvent phase comprises a substantially water immiscible organic solvent, preferably hydrocarbyl or hydrocarbyl halide solvents and mixtures thereof having a boiling point of from about 25° to 250° C. Non-limiting examples of solvents include aromatic solvents such as toluene, xylenes, benzene, mesitylene, and the like and aliphatic solvents such as cyclohexane, hexanes, heptanes, octanes, methylene chloride, methylene bromide, ethylene dichloride, ethylene dibromide, and the like. The lower boiling solvents, can be employed in a closed system.

The proportions of water and organic solvents in the two phase system preferably range from about 0.5 to 10 parts by volume water per part by volume of organic solvent. The proportion of ketone reactant to base preferably ranges from about 0.5 to 5 moles of ketone per mole of base.

The reaction is carried out with mixing to promote contact between the phases at temperatures of from about 50° to 100° C. and preferably from about 70° to 85° C.. Typical reaction times range from about 0.5 to 20 hours.

During the reaction, the cyclopentenone product collects in the organic solvent phase such that product contact with the base is minimized. In this way, product decomposition due to such contact is reduced. Higher base concentrations aid in the "salting out" of the product into the organic phase. When the reaction is complete, the product can be recovered from the organic phase by conventional techniques such as by washing the organic layer with water or aqueous, saturated NaCl and then removing the organic solvent such as by vacuum stripping. The aqueous base layer can be extracted with an organic solvent to recover any product which remains in the aqueous layer.

The invention is further illustrated by, but is not intended to be limited to, the following examples.

EXAMPLE 1

Acetonylacetone (0.20 mol. 22.8g) and toluene (26 ml) were placed in a 100 mL 3-necked, round bottom flask equipped with a thermometer and magnetic stirring bar. A mixture of NaOH (2.0 g, 0.05 mol) and water (20.0 g) was added at 22° C. into the above flask. This two-layer mixture was then stirred and heated at 80°-85° C. for a period of six hours. GC analysis showed a 98% conversion of acetonylacetone. The color of the two-phase mixture was dark brown and some tar formation was observed. The toluene layer was separated and washed once with 10 ml of saturated NaCl solution. The toluene was stripped off at 30°-40° C. (20 mm Hg) and the product 3-methylcyclopent-2-en-1-one was collected by distillation at 45°-70° C. (5-15 mm Hg). The product weighed 9.96 g and GC analysis showed a 92% purity (48% yield) and 8% toluene. The color of product is pale yellow.

EXAMPLE 2

Acetonylacetone (0.10 mol. 11.4g) and $CH_2Br_2$ (40 ml) were placed in a 250 mL 3-necked, round bottom flask equipped with a thermometer and magnetic stirring bar. A mixture of NaOH (4.0 g, 0.10 mol) and water (96.0 g) was added at 22° C. into the flask. This two-layer mixture was stirred at 85° C. over a period of two hours. GC analysis showed a complete conversion of acetonylacetone. The color of this two-phase mixture was dark brown and some tar formation was observed. The $CH_2Br_2$ layer was separated and the aqueous layer was extracted once with $CH_2Br_2$ (10 ml) which was then added to the $CH_2Br_2$ layer. The combined $CH_2Br_2$ solution was washed once with 10 ml of water and then dried over 4A molecular sieves. The $CH_2Br_2$ was stripped off at 30°-40° C. (20 mm Hg) and the product 3-methyl-cyclopent-2-en-1-one was collected at 70°-75° (15 mm Hg). The product weighed 5.44 g (57% yield) and GC analysis showed a 97% purity. The color of product is pale yellow.

What is claimed is:

1. A process for preparing a cyclopentenone, which process comprises forming a two-phase mixture of a 1,4-diketone having the formula $CH_3COCH_2CH_2COCH_2R$, where R is hydrogen or a hydrocarbyl group which contains from 1 to about 15 carbon atoms, a water immiscible organic solvent, said solvent being selected from the group consisting of hydrocarbyl solvents, hydrocarbyl halide solvents and mixtures thereof, and an aqueous base solution, and heating said mixture so as to convert the 1,4-diketone to a cyclopentenone which collects in the organic solvent phase.

2. The process according to claim 1 wherein said R is hydrogen and said cyclopentenone is 3-methylcyclopent-2-en-1-one.

3. The process according to claim 1 wherein said aqueous base solution is an aqueous sodium hydroxide solution.

4. The process according to claim 3 wherein said aqueous base solution is from about a 0.5 to 5 molar aqueous sodium hydroxide solution.

5. The process according to claim 4 wherein said organic solvent has a boiling point of from about 25° to 250° C.

6. The process according to claim 5 wherein the proportions of water and organic solvent range from about 0.5 to 10 parts by volume water per part by volume of organic solvent.

7. The process according to claim 1 wherein said mixture is heated to a temperature of from about 50° to 100° C.

8. The process according to claim 1 wherein the molar proportion of 1,4-diketone to base ranges from about 0.5 to 5 moles of 1,4-diketone per mole of base.

9. A process for making 3-methylcyclopent-2-en-1-one, which process comprises forming a two-phase mixture of acetonyl-acetone in a water immiscible organic solvent, said solvent being selected from the group consisting of hydrocarbyl solvents, hydrocarbyl halide solvents and mixtures thereof, and an aqueous alkali metal base solution and heating said mixture at a temperature of from about 75° to 85° C. so as form 3-methylcyclopent-2-en-1-one which collects in the organic solvent phase.

10. The process according to claim 9 wherein said aqueous alkali metal base solution is 0.5 to 5 molar aqueous sodium hydroxide and said mixture contains from about 0.5 to 5 moles of acetyonylacetone per mole of sodium hydroxide.

11. The process according to claim 10 wherein said organic solvent is selected from toluene and methylene bromide.

* * * * *